United States Patent [19]

Nangle

[11] Patent Number: 4,586,506
[45] Date of Patent: May 6, 1986

[54] ELASTIC WRAP CONNECTING WITH HEAT OR COLD PACK

[76] Inventor: Bruce K. Nangle, 5966 Ellenview Dr., Woodland Hills, Calif. 91367

[21] Appl. No.: 656,185

[22] Filed: Oct. 1, 1984

[51] Int. Cl.⁴ .......................... A61F 7/08; A61F 7/10
[52] U.S. Cl. ............................ 128/403; 128/DIG. 15
[58] Field of Search ............. 128/402, 403, DIG. 15; 62/530, 529

[56] References Cited

U.S. PATENT DOCUMENTS

| | | | |
|---|---|---|---|
| 2,959,938 | 11/1960 | Giardini | 128/403 X |
| 4,055,188 | 10/1977 | Pelton | 128/403 X |
| 4,190,054 | 2/1980 | Brennan | 128/402 |
| 4,470,417 | 9/1984 | Gruber | 128/402 |

FOREIGN PATENT DOCUMENTS

| | | | |
|---|---|---|---|
| 2114033 | 6/1972 | France | 128/403 |
| WO84/02071 | 6/1984 | PCT Int'l Appl. | 128/402 |

*Primary Examiner*—Anton O. Oechsle
*Attorney, Agent, or Firm*—Jack C. Munro

[57] ABSTRACT

An elastic wrap which is to be utilized in connection with a flexible walled container. The flexible walled container includes an access door within which is located either a heat or cold pack. Pad type of attaching means is to be located at a desired location on the elastic wrap which is to connect with a similar type of pad mounted on the container to secure the container to the elastic wrap.

2 Claims, 4 Drawing Figures

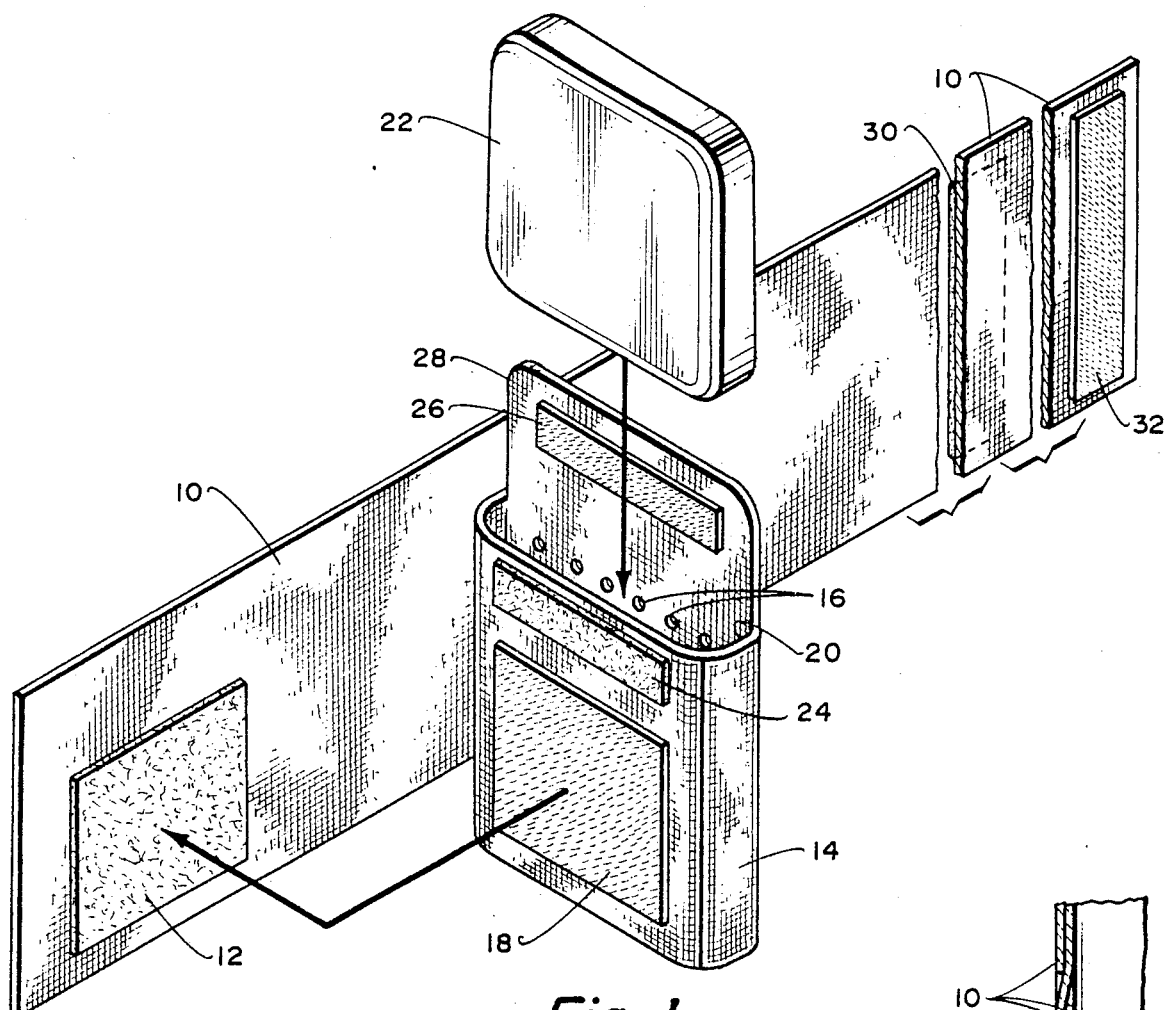
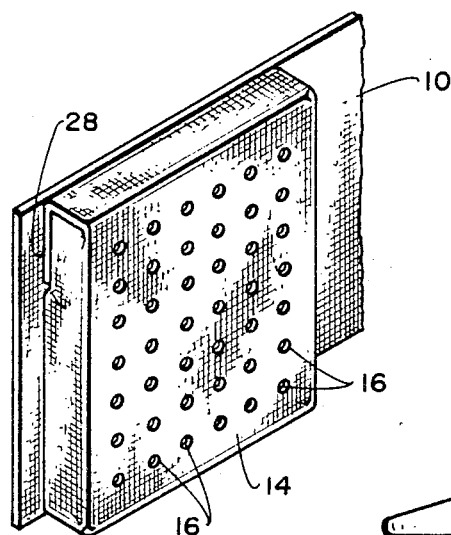
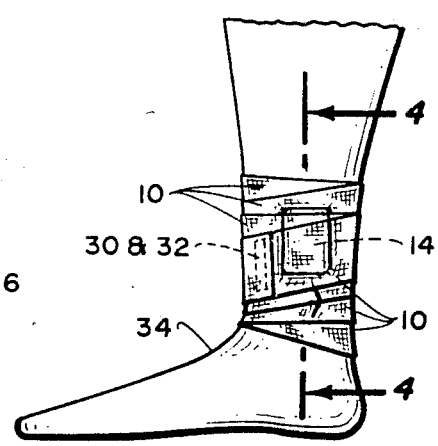
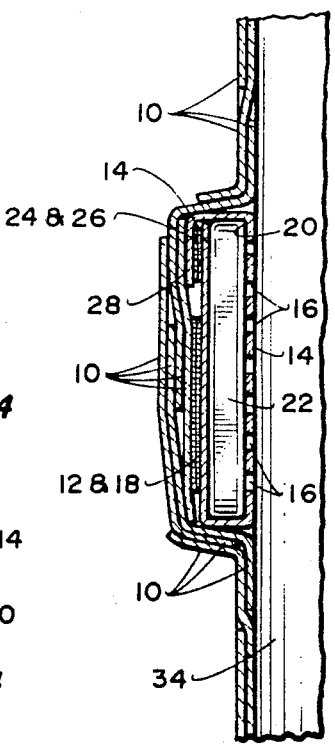
Fig. 1.
Fig. 2.  Fig. 3.  Fig. 4.

ELASTIC WRAP CONNECTING WITH HEAT OR COLD PACK

BACKGROUND OF THE INVENTION

This invention relates to medical devices, and more particularly to an improvement in a heat or cold applying pack to be mounted in conjunction with a conventional elastic wrap which is to be used to wrap onto an injured portion of the human body.

Heat and cold packs for applying such to areas of the human body that have been injured is an exceedingly common method of treatment. This method of treatment is common in conjunction with athletics. Ice packs and heat packs for single patient use come in various sizes. Some are made quite small and others are made larger and designed to wrap around limbs.

It is normally desirable to maintain the application of the heat or cold for a substantial period of time, such as one, two or three hours. It is therefore desirable to utilize some means to fix in position the heat or cold pack at its applied position. In the past it has been common to utilize a connecting snap in conjunction with the pack itself when the pack is in an elongated shape. However, even in such an instance it is hard to precisely secure in position the heat or cold pack without such slipping and moving away from the area to which it is desired the heat or cold be applied.

SUMMARY OF THE INVENTION

Elastic wraps, which are in the form of a stretchable fabric, are in common use and are constructed in rolls. The purpose of an elastic wrap is to provide support for either a limb or portion of the torso of the human body with the elastic wrap wound around the area of the body to which the support is necessary. Because the elastic wrap does stretch a limited amount, if the wrap is wound around a joint, the wrap will "give" as the person normally moves. A heat or cold pack has been designed which is in the form of a container with an open and closable access door. The container has a series of openings on its exterior wall which are to facilitate the conducting from within the container of the heat and cold from either the heat or cold pack that is located within the container. The container includes an attaching pad. Mounted on the elastic wrap is a similar attaching pad. The container is then to be connected by its attaching pad to the attaching pad on the elastic wrap. The container is then placed against the desired portion on the human body to which the heat or cold is to be applied. The operator then proceeds to wrap in a conventional manner the elastic wrap about the human body a number of times until the container is tightly held in position.

BRIEF DESCRIPTION OF THE DRAWING

FIG. 1 is an exploded isometric view of the structure of the present invention showing the heat or cold pack spaced from its container with the container in turn spaced from the elastic wrap;

FIG. 2 is an isometric view showing the heat and cold applying container mounted on the elastic wrap;

FIG. 3 is a diagrammatic view showing a typical application of the structure of this invention onto a portion of a human body; and FIG. 4 is a cross-sectional view taken along line 4—4 of FIG. 3.

DETAILED DESCRIPTION OF THE SHOWN EMBODIMENT

Referring particularly to the drawing, there is shown a conventional elastic wrap 10 which is in the form of an elongated strip and will generally be constructed of a fabric material. It is to be understood that the wrap 10 is designed to stretch a limited amount. Mounted on the wrap 10 directly adjacent the inner end thereof is an attaching pad 12. Let it be assumed that the attaching pad 12 includes a mass of tiny eyelets.

Also fixedly mounted directly adjacent the opposite end of the wrap 10 is a strip 32 which is similar in construction to pad 12. A similar strip 30 is also mounted on the side of the wrap 10 opposite the location of the strip 32. The function of the strips 30 and 32 will be explained further on in this specification.

There is utilized a flexible walled container 14 which normally will be constructed of a fabric or other similar type of material. The container 14 has an exterior wall which has formed therein a mass of tiny openings 16. The size or number or placement of the openings 16 is deemed to be a matter of choice.

Mounted on the interior wall of the container 14 is an attaching pad 18. The attaching pad 18 is constructed to be similar to attaching pad 12 but, instead of having a mass of tiny eyelets, is formed of a mass of tiny hooks. With the pad 18 located in abutment with the pad 12, there is a secure connection established therebetween fixing in position the container 14 to the wrap 10. Also mounted on the inner wall of the container 14 is a strip 24. The strip 24 is similar to pad 12.

The strip 24 is to be connected to a similar strip 26 which is mounted on flap 28 integrally connected to the container 14. The strip 26 is similar to the pad 18. With the strip 26 engaged with strip 24, access into the interior chamber 20 of container 14 is prevented. With the flap 28 in the position shown in FIG. 1 of the drawing, the heat or cold pack 22 can be readily inserted into or removed from the internal chamber 20.

With the heat or cold pack 22 located within the container 20 and strip 26 in contact with strip 24, the container 14 is located so that pad 18 engages with pad 12. The operator then places the container 14 in contact with the injured area of the human body such as the ankle 34 shown in FIG. 3. The operator then proceeds to wind wrap 10 several times about the ankle 34 until on the last wrap the strip 32 can be caused to engage with the strip 30 thereby tightly securing in position the wrap 10. If the wrap 10 is wrapped properly, the container 14 will be tightly held in position directly against the injured area and will be maintained there for the desired period of time.

What is claimed is:

1. In combination with an elastic wrap, said elastic wrap being in the form of an elongated fabric strip, said wrap being capable of a limited amount of stretching, the improvement comprising:

first attaching means mounted on said wrap, said first attaching means comprising a first pad, said first pad comprising a mass of tiny eyelets;

a flexible walled container having an openable access door, said container being adapted to contain a hot or cold pack, said access door being mounted directly against said wrap to assist in preventing accidental opening of said container during the time of usage; and second attaching means mounted on said container, said second attaching means to connect with said first attaching means thereby securing said container to said wrap, said second attaching means comprising a second pad, said second pad comprising a mass of tiny hooks, with said second pad in contact with said first pad a secure connection therebetween occurs, said second pad being disengageable from said first pad, said container is to be located against a portion of the human body and said wrap is then to be wound several times around the human body holding said container in place and providing insulation against escape of the heat or cold substance contained within said container.

2. The combination as defined in claim 1 wherein:
said container having an exterior surface, said exterior surface including a plurality of openings, said openings facilitating the transmission of either heat or cold vapors from within said container against the portion of the human body that it is connected with.

* * * * *